United States Patent [19]

Szántay et al.

[11] Patent Number: 4,464,534
[45] Date of Patent: Aug. 7, 1984

[54] PROCESS FOR THE PREPARATION OF VINCAMINIC ACID ESTERS

[75] Inventors: Csaba Szántay; Lajos Szabó; György Kalaus; János Kreidl; András Nemes; Maria Farkas née Kirják; György Visky; László Czibula, all of Budapest, Hungary

[73] Assignee: Richter Gedeon Vegyeszeti Gyar Rt., Budapest, Hungary

[21] Appl. No.: 425,866

[22] Filed: Sep. 28, 1982

[30] Foreign Application Priority Data

Sep. 30, 1981 [HU] Hungary .................. 2812/81

[51] Int. Cl.³ .................. C07D 461/00; C07D 455/00
[52] U.S. Cl. .................................. 546/51; 546/70
[58] Field of Search .................. 546/51, 70

[56] References Cited

U.S. PATENT DOCUMENTS

| | | | |
|---|---|---|---|
| 3,755,333 | 8/1973 | Szantay et al. | 546/51 |
| 3,770,724 | 11/1973 | Warnant et al. | 546/51 X |
| 4,146,643 | 3/1979 | Pfäffli | 546/51 X |
| 4,283,401 | 8/1981 | Szantay et al. | 424/256 |
| 4,314,939 | 2/1982 | Szantay et al. | 260/239.3 P |
| 4,316,029 | 2/1982 | Rossey | 546/51 |

*Primary Examiner*—Donald G. Daus
*Assistant Examiner*—Diana G. Rivers
*Attorney, Agent, or Firm*—Karl F. Ross; Herbert Dubno

[57] ABSTRACT

The invention relates to a new process for the preparation of apovincaminic acid esters. More particularly, the invention concerns a process for preparing racemic and optionally active vincaminic acid esters of the formula (I)

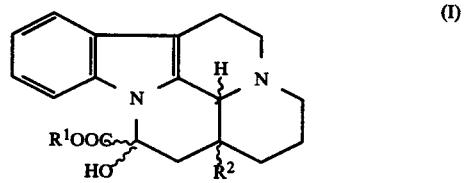

in which $R^1$ and $R^2$ independently stand for alkyl having from one to 6 carbon atoms, and 14-epimers thereof.

According to the invention an octahydroindolo[2,3-a]quinolizine-oxime ester of the formula (II)

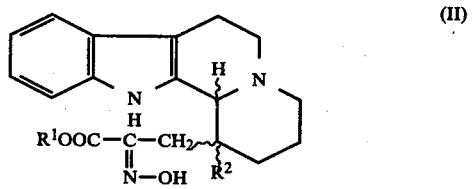

in which $R^1$ and $R^2$ have the same meaning as defined above, is reacted with an aqueous solution of sulfurous acid or a salt thereof at a temperature of 80° to 110° C. and the 14-epimeric mixture obtained is epimerized or separated in a known manner and if desired, the racemic vincaminic acid esters are resolved.

The valuable, pharmaceutically active compounds of the formula (I) can be prepared according to the invention in a considerably improved yield and the undesired side reactions can be suppressed and/or the by-products can easily be converted into other pharmaceutically active materials.

13 Claims, No Drawings

PROCESS FOR THE PREPARATION OF VINCAMINIC ACID ESTERS

The invention relates to a new process for the preparation of vincaminic acid esters. More particularly, the invention concerns a new process for the preparation of racemic and optically active vincaminic acid esters of the formula (I)

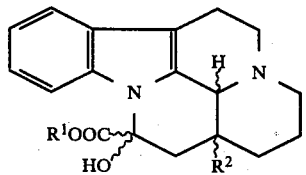
(I)

wherein $R^1$ and $R^2$ independently stand for alkyl having from one to 6 carbon atoms, and 14-epimers of these compounds.

According to the invention an octahydroindolo[2,3-a]quinolizineoxime ester of the formula (II)

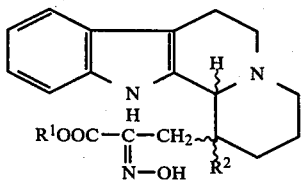
(II)

in which $R^1$ and $R^2$ have the same meaning as defined above, is reacted with an aqueous solution of sulfurous acid or salts thereof, at a temperature of 80° to 110° C. and the 14-epimeric mixture obtained is epimerized or separated in a known manner and if desired, the racemic vincaminic acid esters are resolved.

In the definition of $R^1$ and $R^6$ the term "alkyl having from one to 6 carbon atoms" is used to refer to straight or branched chained alkyl groups having from one to 6 carbon atoms, preferably methyl, ethyl, n-propyl, isopropyl, n-butyl, sec-butyl, tert-butyl, etc.

The compounds of the formula (I) are known in the art and show pharmaceutical activity. In particular the also naturally occurring (+)-vincaminic acid methyl ester and (+)-vincamine are potent cerebral vasodilators.

According to the U.S. Pat. No. 3,770,724 the racemic compounds of the formula (I) are prepared starting from the corresponding racemic octahydroindolo[2,3-a]quinolizine esters by a four-step synthesis. The yields of the subsequent reaction steps are 71%, 61%, 21% and 85%, respectively while the total yield amounts to 7.7% only.

Optically active compounds of the formula (I) can be prepared according to Helv. Chim. 60, 1801 (1977) by a four-step synthesis. Here the subsequent reaction steps can be carried out by the following yields: 83%, 68% and for the last two steps 34%. Accordingly, the total yield is 19%.

By a process disclosed in the Hungarian patent specification No. 175 656 the yield of the last two steps of the latter synthesis was improved to 42% and hence the total yield calculated for the four subsequent reaction steps was increased up to 24%. During the reaction, however, side reactions such as ester hydrolysis, splitting off water, etc. can take place.

All the above processes are disadvantageous in that they comprise relatively many reaction steps which results in a considerably low (at most 24%) total yield.

We have surprisingly found that starting from the compounds of the formula (II) the compounds of the formula (I) can conveniently be prepared in a single reaction step. Taking into account that the compounds of the formula (II) are prepared from the corresponding octahydroindolo[2,3-a]quinolizine esters according to the Hungarian patent application No. 1753/81, the number of the necessary reaction steps is reduced from 4 to 2 relative to the same starting substance. On the other hand under the reaction conditions employed the undesired side reactions, e.g. ester hydrolysis and splitting off water can efficiently be suppressed which results in a substantial increase in yield.

As mentioned above, the compounds of the formula (II) can be prepared starting from octahydroindolo[2,3-a]quinolizine esters, by reaction with tertiary butyl nitrite in an aromatic hydrocarbon solvent, and subsequently with an alkali metal tert-alcoholate and optionally an aprotic dipolar solvent (Hungarian patent application No. 1753/81) with a yield of 80%.

The salts of sulfurous acid used as a reactant in the process according to the invention can be added to the reaction mixture for example in one of the following forms: alkali metal pyrosulfite and water; alkali metal pyrosulfite, water and concentrated sulfuric acid; alkali metal pyrosulfite, water and acetic acid; alkali metal hydroxide, water and sulfur dioxide; an alkali metal salt, e.g. sodium acetate, water and sulfur dioxide; an aqueous solution of sodium sulfite and concentrated sulfuric acid; an alkali metal salt, e.g. sodium acetate, concentrated sulfuric acid and sulfur dioxide, etc. In the above context as an alkali metal for example sodium or potassium may be employed.

The reaction is preferably carried out at a pH between 3.5 and 7. The pH-value can be adjusted by any organic or inorganic acid. Taking into account the solubility relations, sulfuric acid and acetic acid are preferred.

The reaction is performed at a temperature of 80° to 110° C., preferably 85° to 95° C., under atmospheric pressure or an overpressure of 0.1 to 0.5 atm.

The process according to the invention yields a 14-epimeric mixture which may be epimerized by an alkali metal alcoholate in a manner known per se or the epimers may be separated by suitable solvents.

In the starting compounds of the formula (II) the $R^2$ group in the 1-position and the 12b-hydrogen atom can be in cis ($\alpha,\alpha$ or $\beta,\beta$) or trans ($\alpha,\beta$ or $\beta,\alpha$) configuration relative to each other. This configuration does not change during the reaction, i.e. remains the same also in the end products.

Starting from racemic compounds of the formula (II), racemic compounds of the formula (I) are obtained, while optically active starting materials lead to optically active end products. If desired, a racemic end product can be resolved by any of the known methods.

The main advantage of the new process according to the invention consists in the fact that by reducing the number of the necessary reaction steps from four to two (related to the same starting material) a 2.5 to 7.5-times increase in yield is achieved. As to its industrial application, a further advantage is that the by-products if formed, can be converted into the corresponding pharmaceutically active apovincaminic acid esters.

Further details of the invention are illustrated by the following Examples which are for illustration and not for limitation of our invention.

REFERENCE EXAMPLE (−)-1β-[(2′-Methoxycarbonyl-2′-hydroxyimino)ethyl]-1α-ethyl-1,2,3,4,6,7,12,12bα-octahydroindolo[2,3-a]quinolizine and its hydrochloride To 34 g. (0.1 moles) of (−)-1β-(2′-methoxycarbonylethyl)-1α-ethyl-1,2,3,4,6,7,12,12bα-octahydroindolo[2,3-a]quinolizine 20 ml. of absolute toluene, a 55 to 60% toluene solution of 30 ml. of tert.-butyl nitrite and then 17 g. (0.15 moles) of potassium tert.-butylate are added. The mixture is stirred at 25° to 30° C. for 20 minutes, 150 ml. of absolute methanol are slowly added and the mixture is stirred at 40° C. for 3 hours. The reaction mixture is then cooled to 20° C., is acidified up to pH=1 with concentrated hydrochloric acid, 50 ml. of water are added and the mixture is stirred at +5° C. for 2 hours. The precipitate is filtered off, the KCl is washed out with water and the precipitate is dried. 32.5 g. (80%) of hydrochloride of the title compound are obtained, melting at 265° to 272° C. with decomposition.

$[\alpha_D^{20}] = -57°$ (c=1, DMF).

From the hydrochloride obtained the free base is prepared by suspending the salt in 80 ml. of methanol and adding a mixture of 25 ml. of 25% aqueous ammonium hydroxide solution and 40 ml. os water dropwise, with stirring. After one hour stirring it is cooled to 10° C., filtered, washed with water and dried. 24 to 25 g. of the title compound are obtained, melting at 208° to 210° C.

$[\alpha_D^{20}] = -62°$ (c=1, DMF).

EXAMPLE 1

(+)-Vincamine

A mixture of 22 g. (0.06 moles) of (−)-1α-ethyl-1β-(2′-methoxycarbonyl-2′-hydroxyiminoethyl)-1,2,3,4,6,7,12,12bα-octahydroindolo[2,3-a]quinolizine (Hungarian patent application No. 1753/81), 20 ml. of acetic acid, 100 ml. of water and 12 g. of sodium pyrosulfite is stirred at 90° to 92° C. for 6 hours. The reaction mixture is allowed to cool and its pH is adjusted to 9 by concentrated aqueous ammonium hydroxide solution. The alkaline solution is extracted with two 60-ml. portions of dichloromethane. The dichloromethane solution is evaporated to dryness and the residue is refluxed with 50 ml. of a 2% methanolic potassium methylate solution for two hours. The mixture is then allowed to stand at 0° C. for two hours whereupon the precipitated (+)-vincamine crystals are filtered off, washed with two 10-ml. portions of methanol and dried at 60° C. 13.7 g. (65%) of the title compound are obtained.

$[\alpha]_D^{20} = +41°$ (c=1, pyridine).

Melting point: 234° to 235° C. (chlorobenzene).

EXAMPLE 2

(+)-Vincamine

A mixture of 36.9 g. (0.1 moles) of (−)-1α-ethyl-1β-(2′-methoxycarbonyl-2′-hydroxyiminoethyl)-1,2,3,4,6,7,12,12bα-octahydroindolo[2,3-a]quinolizine (Hungarian patent application No. 1753/81), 16.8 ml. of acetic acid, 250 ml. of water, 5.8 ml. of concentrated sulfuric acid and 75 g. of sodium pyrosulfite are stirred at 90° C. for 7 hours. After cooling, the pH of the mixture is adjusted to 9 by 60 ml. of a concentrated aqueous ammonium hydroxide solution. The alkaline solution is extracted with 200 ml. and subsequently 100 ml. of dichloromethane. Dichloromethane is distilled off from the combined dichloromethane extracts, to the distillation residue 100 ml. of a 2% methanolic potassium methylate solution are added and the mixture is refluxed for 4 hours. The reaction mixture is then cooled, allowed to stand at 0° C. for one hour, filtered and the solid is washed with two 30-ml. portions of methanol and subsequently dried at 60° C. 26.6 g. (75%) of the title compound are obtained.

$[\alpha]_D^{20} = +41°$ (c=1, pyridine).

Melting point: 234° to 235° C. (chlorobenzene).

The filtrate (mother liquor of epimerization) is evaporated to dryness, to the residue 16 ml. of ethanol, 20 g. of dry p-toluene-sulfonic acid and 120 ml. of toluene are added. The mixture is boiled and 80 ml. of the solvent are distilled off. The mixtur is then refluxed for two hours. The reaction mixture is cooled to 10° C., 50 ml. of toluene and 50 ml. of water are added and the pH is adjusted to 9 by a concentrated aqueous ammonium hydroxide solution. The toluene layer is separated and the ayueous layer is extracted with 50 ml. of toluene. The combined toluene solutions are dried with anhydrous solid sodium sulfate, filtered and the filtrate is decolored with 1 g. of Brockmann alumina. The solution is then concentrated to 20 ml., a solution of 0.6 g. of potassium tert-butylate in 40 ml. of ethanol is added and the mixture is refluxed for one hour. The reaction mixture is evaporated to 20 ml., cooled to 10° C., the precipitated crystals are filtered off, washed with two 10-ml. portions of ethanol and dried. 3.5 g. of (+)-apovincaminic acid ethyl ester are obtained, melting at 145° to 147° C.

Yield: 10% related to the starting substance.

$[\alpha]_D^{20} = 141°$ (c=1, chloroform).

EXAMPLE 3

(±)-Vincamine

A mixture of 36.9 g. (0.1 moles) of (±)-1α-ethyl-1β-(2′-methoxycarbonyl-2′-hydroxyiminoethyl)-1,2,3,4,6,7,12,12bα-octahydroindolo[2,3-a]quinolizine (Hungarian patent application No. 1753/81), 16.8 ml. of acetic acid, 250 ml. of water, 15 ml. of concentrated sulfuric acid and 46.5 g. of sodium sulfite is stirred at 90° C. for 6 hours. After cooling the pH is adjusted to 9 by 60 ml. of a concentrated aqueous sodium hydroxide solution, and the alkaline solution is extracted with two 100-ml. portions of dichloromethane. From the combined dichloromethane extracts dichloromethane is distilled off, to the residue 110 ml. of a 2% methanolic potassium methylate solution are added and the mixture is refluxed for 4 hours. The reaction mixture is cooled to 0° C., the precipitated crystals are filtered off, washed with two 30-ml. portions of methanol and dried at 60° C. 20.8 g. (59%) of the title compound are obtained.

Melting point: 234° to 235° C. (chlorobenzene).

EXAMPLE 4

(+)-Vincamine

In a 2-lit. enamelled autoclave into a mixture of 50 g. of (−)-1α-ethyl-1β-(2′-methoxycarbonyl-2′-hydroxyiminoethyl)-1,2,3,4,6,7,12,12bα-octahydroindolo[2,3-a]quinolizine (Hungarian patent application No. 1753/81), 82 g. of sodium acetate, 700 ml. of water and 15 ml. of concentrated sulfuric acid 64 g. of sulfur dioxide gas are introduced, whereupon the equipment is sealed and kept at 80° to 90° C., under an overpressure of 0.2 to 0.3 atm. for 5 hours. Upon cooling the equipment is opened, 130 ml. of concentrated aqueous ammonium hydroxide solution are added to the reaction mixture and the alkaline solution is extracted with two 200-ml. portions of dichloromethane. The combined dichloromethane layers are evaporated to dryness and the evaporation residue is refluxed with 150 ml. of a 2% methanolic potassium methylate solution for 4 hours. The mixture is cooled, the precipitated crystals are filtered off, washed with two 30-ml. portions of methanol and dried at 60° C. 29 g. (60.5%) of the title compound are obtained.

Melting point: 234° to 235° C. (chlorobenzene).
$[\alpha]_D^{20} = 42°$ (c=1, pyridine).

EXAMPLE 5

(+)-Vincaminic acid ethyl ester

The procedure described in Example 2 is followed except that as a starting material 38.3 g. (0.1 moles) of (−)-1α-ethyl-1β-(2'-ethoxycarbonyl-2'-hydroxyiminoethyl)-1,2,3,4,6,7,12,12bα-octahydroindolo[2,3-a]quinolizine (Hungarian patent application No. 1753/81) are employed. The epimerization is carried out with a corresponding amount of ethanolic potassium methylate solution. 27.4 g. (74%) of the title compound are obtained.

Melting point: 238° to 240° C.

To the mother liquor of epimerization 20 g. of dry p-toluenesulfonic acid are added and the mixture is evaporated to 50 ml. To the concentrated solution 150 ml. of toluene are added, whereupon 75 ml. of the solvent are distilled off while the inner temperature rises up to 110° C. The reaction mixture is then refluxed for two hours, subsequently cooled to 10° C., 50 ml. of toluene and 50 ml. of water are added and the pH is adjusted to 9 by a concentrated aqueous ammonium hydroxide solution. The toluene layer is separated, the aqueous layer is extracted with 50 ml. of toluene and the combined toluene extracts are dried with solid, anhydrous sodium sulfate, filtered and the filtrate is decolored with 5 g. of Brockmann alumina. The filtrate is then evaporated to 20 ml., to the residue 50 ml. of ethanol are added 25 ml. of which are distilled off. The mother liquor is cooled to 10° C. The precipitated crystals are filtered off, washed with two 10-ml. portions of ethanol and dried. 3.9 g. (11% related to the starting substance) of (±)-apovincaminic acid ethyl ester are obtained.

Melting point: 142° C.

EXAMPLE 6

(+)-Trans-vincamine(3β,16α) and
(+)-trans-14-epivincamine(3β,16α)

A mixture of 51 g. (0.15 moles) of (−)-trans-1α-ethyl-1β-(2'-methoxycarbonyl-2'-hydroxyiminoethyl)-1,2,3,4,6,7,12,12bβ-octahydroindolo[2,3-a]quinolizine (Hungarian patent application No. 1753/81), 600 ml. of water, 50 ml. of acetic acid, 7.5 ml. of concentrated sulfuric acid and 20 g. of sodium pyrosulfite is stirred at 92° C. for two hours. A further 10-g. portion of sodium pyrosulfite is added to the mixture which is then stirred at 92° C. for another 4 hours. The solution is cooled to 20° C., 200 ml. of chloroform are added and the pH is adjusted to 9 with a 20% aqueous sodium hydroxide solution. After stirring for one minute the layers are separated and the aqueous layer is extracted with 100 ml. of chloroform. The chloroform solution is dried with solid, anhydrous sodium sulfate, filtered and the filtrate is evaporated to dryness in vacuo. To the evaporation residue 50 ml. of methanol are added, the mixture is boiled for 2 minutes and allowed to stand at 0° C. for one hour. The precipitated crystals are filtered off, washed with three 20-ml. portions of methanol and dried.

30 g. of a white, crystalline material are obtained consisting of a mixture of (+)-trans-vincamine and (+)-trans-14-epivincamine.

The mixture is refluxed with 40 ml. of chloroform for two minutes and is allowed to stand at 0° C. for two hours. The precipitate is filtered off and washed with two 10-ml. portions of chloroform having a temperature of 0° C. 15 g. of a substance enriched in (+)-vincamine are obtained. The product is refluxed in 40 ml. of chloroform, allowed to stand at 0° C. for one hour, the precipitated substance is filtered off, washed with cool chloroform and dried.

10 g. (19%) of pure (+)-trans-vincamine(3β,16α) are obtained.

Melting point: 189° to 190° C.
$[\alpha]_D^{20} = +89°$ (c=1, chloroform).

The chloroform filtrates are combined, evaporated to dryness in vacuo, the residue is dissolved in 20 ml. of chloroform, the solution is diluted with 60 ml. of methanol and allowed to stand for two hours at 0° C. The precipitated crystals are filtered off and washed with two 10-ml. portions of methanol. 12 g. of a material enriched in (+)-trans-14-epivincamine are obtained. The substance is dissolved in 20 ml. of hot chlorofom, the solution is diluted with 50 ml. of methanol and allowed to stand at 0° C. for 2 hours. The precipitated crystals are filtered off, washed with two 5-ml. portions of methanol and dried. 8 g. (15%) of (+)-trans-14-epivincamine are obtained, melting at 167° to 168° C.

$[\alpha]_D^{20} = +36.5°$ (c=1, chloroform).

We claim:

1. A process for the preparation of a racemic or optically active compound of the formula (I)

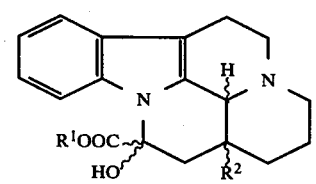

(I)

wherein $R^1$ and $R^2$ independently stand for $C_1$ to $C_6$ alkyl, or a 14-epimer thereof, which comprises the steps of (a) reacting a compound of the formula (II)

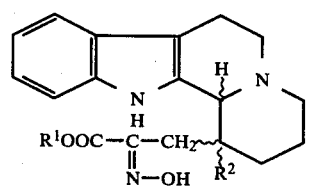

(II)

with an aqueous solution of sulfurous acid or a salt thereof at a temperature of 80° to 100° C. to form a mixture of the compound of the formula (I) and its 14-epimer; and (b) epimerizing the mixture formed in step (a) to yield the compound of the formula (I) or separating out the 14-epimer from the compound of the formula (I) to obtain the desired product.

2. The process defined in claim 1, further comprising the step of (c) resolving any of the compound of the formula (I) obtained in racemic form to obtain the corresponding optically active isomers.

3. The process defined in claim 1, step (a), carried out at a pH between 3.5 and 7.

4. The process defined in claim 1, step (a), wherein the sulfurous acid salt is an alkali metal pyrosulfite in water.

5. The process defined in claim 4 carried out in the presence of an organic acid or an inorganic acid.

6. The process defined in claim 5 wherein the organic acid is acetic acid and the inorganic acid is sulfuric acid.

7. The process defined in claim 1, step (a), wherein the sulfurous acid salt in aqueous solution is formed by adding sulfur dioxide, and an alkali metal hydroxide or salt to water.

8. The process defined in claim 7 carried out in the presence of an organic acid or an inorganic acid.

9. The process defined in claim 8 wherein the organic acid is acetic acid and the inorganic acid is sulfuric acid.

10. The process defined in claim 7 wherein the alkali metal salt is sodium acetate.

11. The process defined in claim 1, step (a), wherein the sulfurous acid salt in aqueous solution is sodium sulfite.

12. The process defined in claim 11 carried out in the presence of an organic acid or an inorganic acid.

13. The process defined in claim 12 wherein the organic acid is acetic acid and the inorganic acid is sulfuric acid.

* * * * *